United States Patent [19]

Barkalow

[11] 3,985,126

[45] Oct. 12, 1976

[54] PATIENT RETENTION AND SUPPORT

[75] Inventor: Clare E. Barkalow, Comstock Park, Mich.

[73] Assignee: Michigan Instruments, Inc., Grand Rapids, Mich.

[22] Filed: Feb. 7, 1975

[21] Appl. No.: 547,872

[52] U.S. Cl. .......... 128/53
[51] Int. Cl.$^2$ .......... A61N 7/00
[58] Field of Search .......... 128/50–53, 128/28, 24 R

[56] References Cited

UNITED STATES PATENTS

| | | | |
|---|---|---|---|
| 3,277,887 | 10/1966 | Thomas | 128/53 |
| 3,291,124 | 12/1966 | Jennings et al. | 128/53 |
| 3,610,233 | 10/1971 | Barkalow | 128/53 |
| 3,804,082 | 4/1974 | Tarjan et al. | 128/51 |
| 3,870,038 | 3/1975 | Arblaster | 128/28 |

*Primary Examiner*—Lawrence W. Trapp
*Attorney, Agent, or Firm*—Price, Heneveld, Huizenga & Cooper

[57] ABSTRACT

The support and retention includes an upper back supporting portion spaced in part at least from the base providing a clearance opening for insertion of a mechanical compressor platform without requiring movement of the patient. Preferably, the clearance opens to both sides to permit insertion of the platform from either side and the upper portion is also preferably saddle-shaped and inclined upwardly to permit downward sloping of the head to provide patency of the breathing canal.

20 Claims, 6 Drawing Figures

PATIENT RETENTION AND SUPPORT

BACKGROUND OF THE INVENTION

1. Field of Invention

This invention relates to a unique patient retention and support assembly particularly designed to facilitate and accommodate existing external cardiac compressors as well as accommodating manual preliminary cardiopulmonary resuscitation.

II. Description of the Prior Art

Existing mechanical cardiac compressors have been extremely successful in treating patients in various phases of cardiac arrests. Such a cardiac compressor is illustrated in FIGS. 1 and 2 of the drawings and briefly, includes a support platform 12 positionable beneath the patient's back. Preferably, the lower sternum of the patient is centered over the platform so that it provides full support for operation of the compressor system. A compressor sub-assembly 16 includes a post 18 and base attachment 20 which is preferably detachable from platform 12 so that the latter can be inserted beneath the patient prior to mounting the compressor sub-assembly thereon. This, of course, facilitates positioning the platform under various types of patients.

FIGS. 5 and 6 illustrate in part a combination cardiac compressor and pulmonary ventilation system 10*a* illustrated in fully assembled operative fashion in FIG. 6. Such a system is similar to the compressor illustrated in FIGS. 1 and 2 and like reference numerals are utilized to illustrate similar parts with the suffix *a*. The system 10*a* of course is designed to provide pulmonary ventilation in addition to resuscitation. A quick disconnect plate bar 22 is shown in FIG. 5 with an actuating handle 24 manipulative to disconnect sub-assembly 16*a* or conversely provide quick attachment thereto. External cardiac compressors and combination pulmonary ventilation systems of the type illustrated in the drawings are illustrated and described in detail in Applicant's prior issued, commonly assigned U.S. Pat. No. 3,364,924 entitled PNEUMATICALLY OPERATED CLOSED CHEST CARDIAC COMPRESSOR dated Jan. 23, 1968; U.S. Pat. No. 3,364,925 entitled EXTERNAL CARDIAC COMPRESSOR likewise date Jan. 23, 1968; and U.S. Pat. No. 3,461,860 entitled PULMONARY VENTILATION SYSTEM AND COMBINATION CARDIAC COMPRESSOR AND VENTILATION SYSTEM dated Aug. 19, 1969.

There is a growing recognition of the need for and the importance of mechanical cardiopulmonary resuscitative support for the cardiac arrest patient in certain environments. One of these environments is the patient in ambulance transport. In the standard ambulance, a cardiopulmonary resuscitator (CPR) is the only practical approach available for dealing with cardiac arrests. In the fully sophisticated "Cardiac Vans", it is frequency needed for: (1) refractory cardiac arrest patients, who are non-responsive to the early attempts at definitive therapy, and (2) patients who have been in cardiac arrests for over one minute without support, and who will frequently require extended supportive therapy to improve myocardial tone before definitive therapy in the form of drugs and electrical defibrillation, can be successful. In such cases, there is a frequent need to maintain the highest possible levels of CPR support with the patient in transport.

CPR's of the type described above are ideally suited for this purpose as they were specifically designed for ambulance application, and are being widely and very successfully utilized. While in certain instances a support platform 12 such as that referred to in FIG. 1 is both feasible and practical for the patient in transit under CPR support on a standard ambulance cot without any restraints or auxiliary equipment whatsoever, there are situations where a system of restraint for the cardiac compressor-patient-cot system can be very helpful. These situations would include: (1) instances where mechanical CPR support would be started with the patient on an ambulance cot remote from the ambulance and where return of the cot with the patient involves more than rolling the cot back over relatively smooth terrain—e.g. down or up stairways, or over rough terrain, or in congested situations; and (2) instances where the subsequent travel of the ambulance is over unusually rough terrain, or over tortuous roadway. Ideally, such a restraint system should meet the following specifications: (1) the restraint system should tie all three elements of the system—mechanical compressor, patient and cot—together, one hundred percent of the time, as an integral system, sufficient to inhibit significant relative motion between any two parts of the system. The restraint should be adequate for plus or minus one gravitational force of lateral accelleration which is equivalent to a 45° tilt of the ambulance cot; (2) the restraint provided to meet (1) above must not restrict the patient's chest in any way. Normal chest spring-back following each compression cycle, and normal chest rise during each ventilation cycle must remain completely uninhibited; (3) the restraint system must be quickly and easily applied, covering a wide range of patient sizes, pediatric to very large patients; (4) the restraint system must in no way detract from the normal speed and/or ease of applying the CPR to a patient, and must permit its application from either the right or left side of the patient; and (5) the restraint system should be usable with preliminary manual CPR—providing good back support and head extensions for the manual technique even before the mechanical equipment is applied. Easy access for introduction of the mechanical equipment must thus be provided without having to remove the patient from the support while the mechanical CPR is brought into position for utilization.

Applicant is unaware of any prior art designed to accomplish the foregoing objectives. Heretofore, it has not been thought to provide a support device beneath the patient which permitted insertion of a CPR platform without moving the patient. Basically, the only retention system utilized was that of a strap on either the ambulance stretcher or cot. However, none of the prior art approaches met the needs specified above, and thus there is a genuine need in this art for an improved patient support and retention system.

SUMMARY OF THE INVENTION

In accordance with the invention, a portable patient retention and support capable of utilization for manual resuscitation includes an upper back support portion having a portion spaced from the base of the support forming a clearance opening to permit insertion of the platform of a mechanical resuscitator. In this fashion, a patient can be properly supported for manual resuscitation and if necessary, without moving the patient, a mechanical CPR platform can be inserted beneath the patient in the clearance provided between the upper support portion and base so that mechanical assistance can be utilized. Preferably, the retention and support has a low profile and the clearance opening extends laterally through the retention to permit insertion of the CPR platform from either side.

In other and narrower aspects of the invention, the upper support portion is saddle-shaped to facilitate proper positioning of the patient and the support includes both straps in the base to secure it firmly to a cot, stretcher or the like and straps in the saddle portion for positioning over the shoulders of the patient to anchor the patient positively to the retention and cot without impeding the chest area. The saddle portion is preferably inclined so that the patient's head pivots rearwardly when positioned on the retention to improve patency of the breathing canal. Other aspects of the invention include guide means formed in the clearance opening to assist insertion of a CPR platform and stop and support means to secure it properly laterally relative the retention so that when the compressor is actuated, it is positioned properly over the patient. The entire retention support is preferably comprised of a durable plastic which is both economical and provides adequate service life without degradation in the appearance of the support.

The advantages provided by the subject invention summarized above are multi-fold. For the first time, all of the requirements for an ideal patient restraint system are met for the patient in transport under mechanical CPR. The retention and support can be left in place on the ambulance cot for example as it is comfortable and hardly detectable under the patient's back due to its preferred low profile. This is particularly true if a head pillow is used as would normally be the case in non-cardiac emergency. Alternatively, it can be easily removed and stored under the cot pad. It is also significant to note that the retention and support is highly desirable for utilization in a more stationary environment compared to ambulance emergency such as in the hospital itself. It can easily be stored in a convenient place or hung on a wall and yet is available for quick utilization in cases where it is anticipated that either manual or mechanical resuscitation will be required. In such cases, it becomes very quick and easy to insert the platform of a CPR in the retention support without having to physically move or inconvenience the patient. In a stationary environment, such as in hospital use, the strapping may not be needed, and may be removed. The sloped orientation of the saddle support area where the back rests not only helps center the patient, but the upward inclination at the head end permits rearward inclination of the head relative the body to increase patency of the breathing canals. Thus, a completely improved patient support is provided which is now capable of utilization with manual CPR, and in cooperation with a mechanical CPR which has not heretofore been known. Further, the cooperation with a mechanical CPR improves the speed and operation of the CPR without affecting the patient's status.

DESCRIPTION OF THE PREFERRED EMBODIMENT

Figure 3:
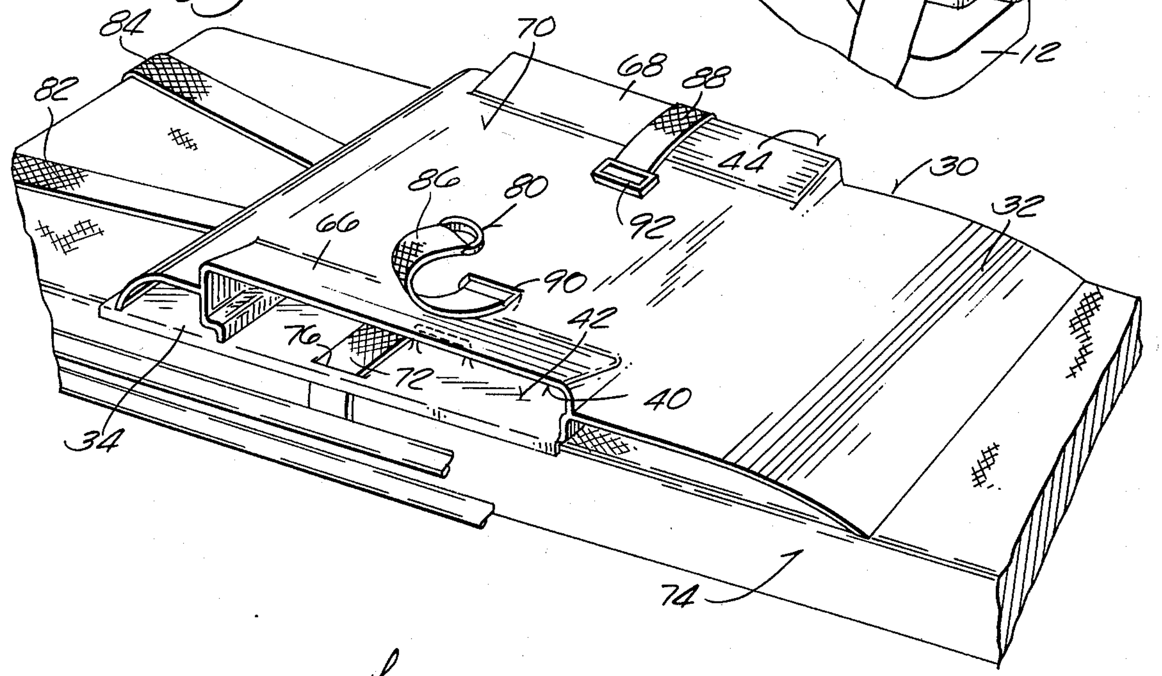
FIG. 3 is a fragmentary perspective view of a stretcher or hospital bed with the novel patient retention and support of the invention secured thereto.

Referring now to the drawings in detail, and in particular to FIG. 3, the retention and support 30 includes an upper back support portion 32 and base portion 34. An intermediate member 36 (FIG. 4) connects the upper portion 32 and base 34 together in spaced relationship defining a tunnel-like opening 40 extending laterally through support 30 terminating in a pair of spaced inlets 42 and 44 (FIG. 3). The tunnel-like opening 40 is adapted to receive a compressor platform such as platform 12 or **12*a* on either side of support 30**.

Figure 4:
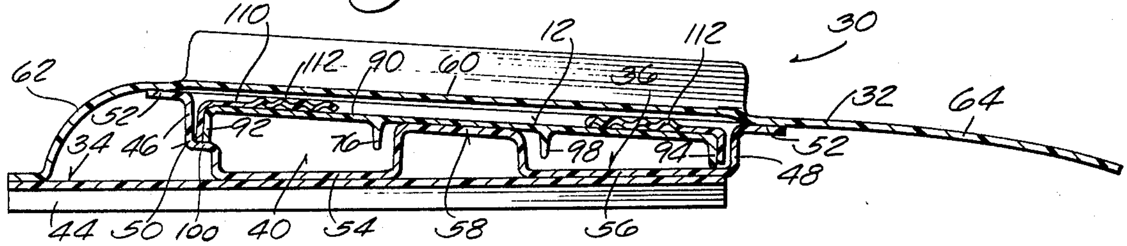
FIG. 4 is a side elevation view in cross section of the patient retention and support of the invention.

Referring to FIG. 4, base portion 34 is comprised of a flat, preferably plastic plate-like member and includes a downwardly depending flange 44 along each lateral edge. These flanges act as edgings to locate the assembly on a standard ambulance cot mattress. Alternatively, on a hospital bed they tend to imbed in the mattress to provide better stabilization of position. Intermediate member 36 has a general U-shaped opening upwardly. One leg 46 is higher than the other leg 48 and includes an offset 50 the significance of which will be described hereinafter. Each of the legs 46 and 48 include an outwardly extending flange 52 which is secured to the interior surface of the upper back support portion 32. The central body portions 54 and 56 of intermediate member 36 are flat and connected to the platform portion of base 34. The central portion of intermediate member 36 is disrupted at 58, the significance of which will also be described hereinafter.

Figure 6:
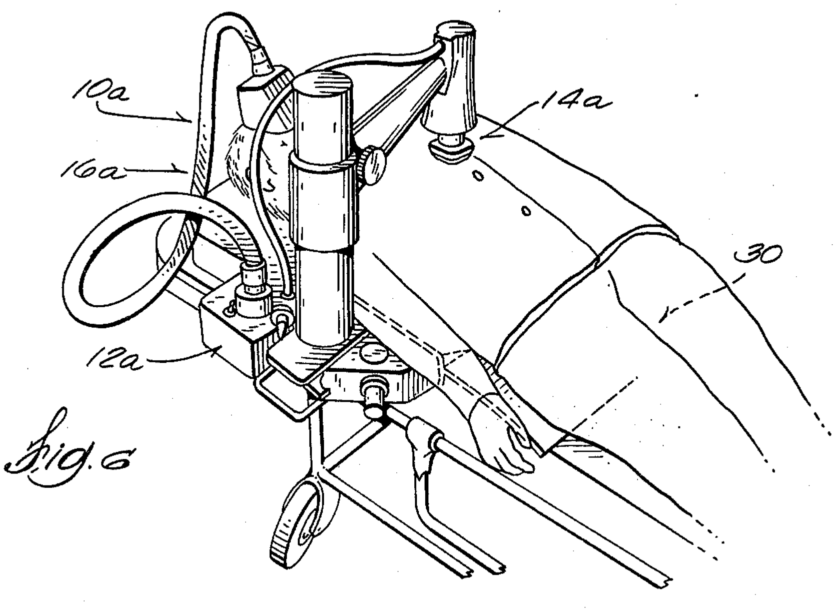
FIG. 6 is a fragmentary perspective view of a patient being treated with a pulmonary ventilation system and combination cardiac compressor and ventilation system on a portable hospital bed with the patient retention and support of the invention.

The upper back support portion 32 has an essentially flat central portion 60 and a curved head portion 62 with a more tapered less definitive curved tail portion 64. Due to the difference in extension of legs 46 and 48 of intermediate member 36, back support portion 32 is supported by base 34 at an incline wherein the head portion is elevated relative the tail portion. In this fashion, a patient supported on the patient retention and support 30 is positioned such that his shoulders are elevated relative the remainder of his body with the head being supported in a downwardly inclined fashion as illustrated for example in FIG. 6.

Referring to FIG. 3, upper back support portion 32 preferably includes laterally raised portions 66 and 68 forming a saddle 70 for receipt of the patient. The saddle assists proper placement of the patient and tends to center the patient laterally with respect to the support for either manual cardiac compression or mechanical compression. A natural index for the patient is thus provided by placing the patient's head over the abruptly curved portion 62 of the back support portion, the saddle 70 providing a natural centering of the patient's body so that when utilized in connection with a pneumatic cardiac compressor 10, system 14 will be centered over the lower sternum for effective compression.

Figure 5:
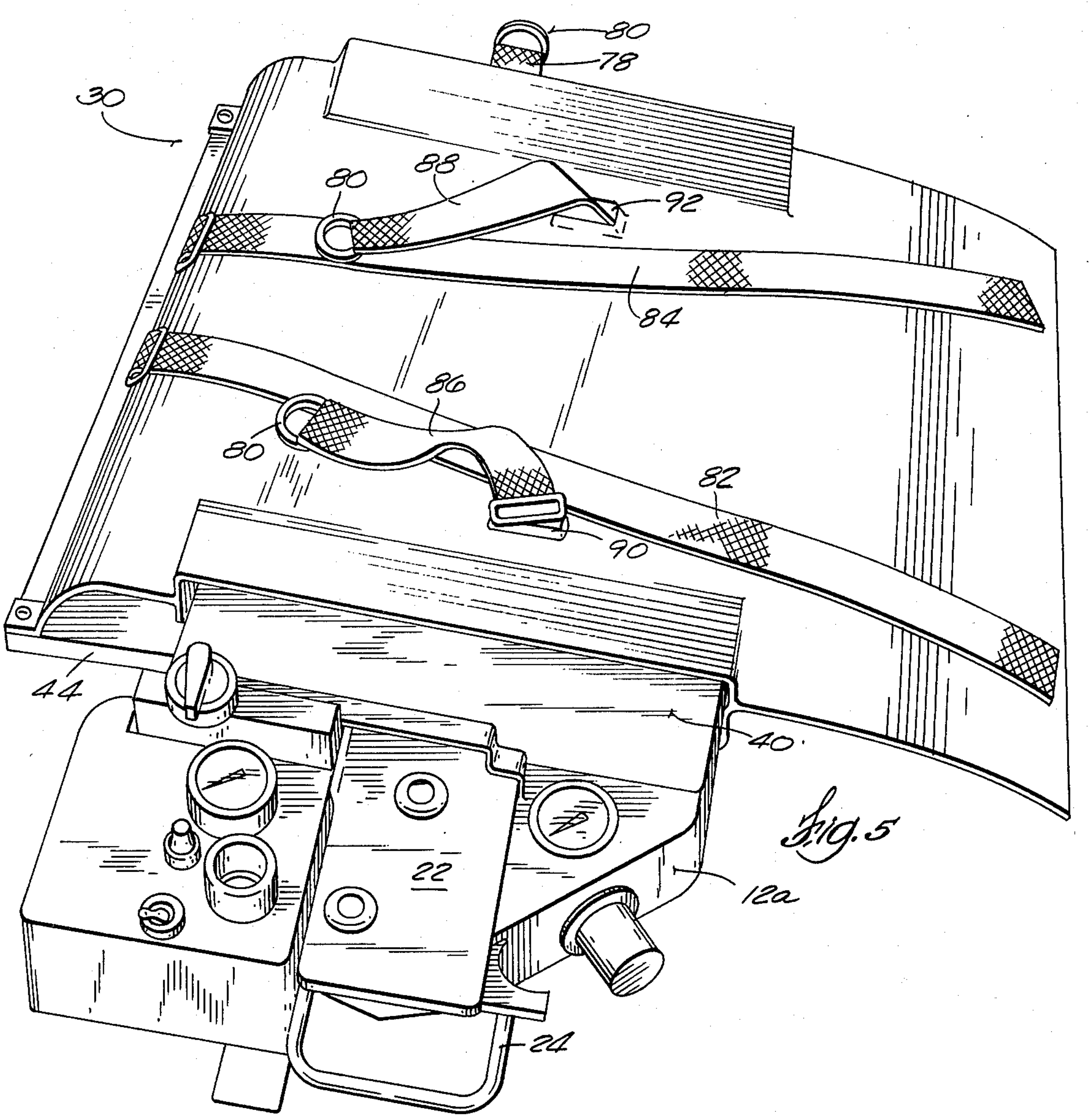
FIG. 5 is a perspective plan view of the base portion of a cardiac compressor with the platform portion inserted in the patient retention and support of the invention.

A strap 72 (FIG. 3) is provided for easy and positive attachment of support and retention 30 to an ambulance cot, stretcher, or hospital cot 74. The strap lays flat on the floor of base 34 and extends through a pair of openings only one opening 76 of which is illustrated in FIG. 3. One end of the strap forms the tongue portion of the strap while the other end 78 (FIG. 5) includes a double-D ring arrangement 80 permitting quick connection-disconnection during emergency situations. Strap 72 thus positively affixes the support retention 30 as desired to a body support device 74.

Figure 1:
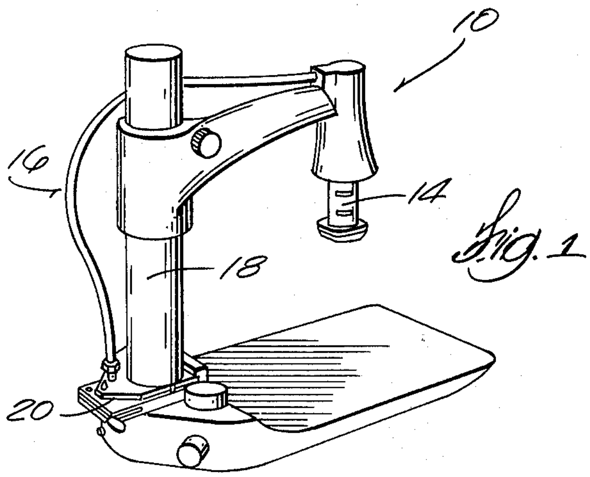
FIG. 1 is a perspective view of a pneumatically operated closed chest cardiac compressor.
Figure 2:
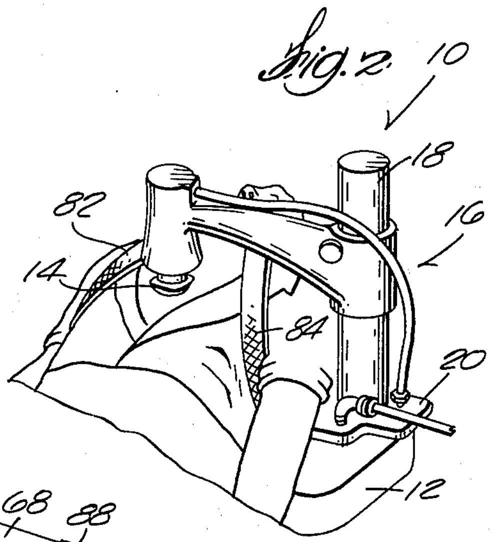
FIG. 2 is a fragmentary perspective view illustrating the compressor in FIG. 1 being utilized on a patient in conjunction with the retention system.

Additional straps are provided to secure the patient positively to support and retention 30. A pair of forwardly extending shoulder straps 82 and 84 (FIGS. 2, 3 and 5) are anchored at one end to the forward end of support and retention 30 and free at their opposite end for engagement with straps 86 and 88 respectively. The latter straps are anchored at one end through openings 90, 92 provided through the saddle portion 70 of upper back support portion 32 and include double-D ring arrangements 80 at their free end. As will be readily discerned from FIGS. 2, 3 and 5, straps 80 and 82 are connected to each other while straps 84 and 88 are likewise connected to each other on opposite sides of the patient over his shoulders securing him to support and retention 30 without limiting normal movement of the chest for resuscitation. The restraint system comprising the straps described hereinbefore tie all three elements of the system together. Namely, the cot or stretcher 74, the support and retention 30 and the patient. As will be described hereinafter, this also includes in the stabilization, a mechanical compressor when desired. Thus, the three elements plus the resuscitator are tied together 100% of the time as an integral system, and in the embodiment illustrated it is sufficient to inhibit significant relative motion between any two parts of the system. The restraint has proven adequate to withstand lateral acceleration of plus or minus one gravitational force which is essentially equivalent to a 45° tilt of an ambulance cot or stretcher. Of significance, this is done without restraining normal chest spring-back following each compression cycle, and normal chest rise during each ventilation cycle. The restraint system is quickly and easily applied covering a wide range of patient sizes, from pediatric to very large patients.

Referring now to FIGS. 3 and 4, the raised portions 66 and 68 forming saddle 70 also form the upper roof portion of inlets 42 and 44. In effect, they form a cam-type opening for receipt of the free end of the cardiac compressor platform such as platforms 12 or 12*a*. Thus, with a patient secured to support and retention 30 which is in turn secured to the cot or stretcher, a support platform can be quickly inserted into tunnel-like opening 40 through either inlet 42 or 44 and the enlarged inlets provide a positive means of camming the end of platforms 12 or 12*a* into and through tunnel 40.

A preferred platform configuration 12 is illustrated in FIG. 4. The configuration shown includes a central flat body portion 90 having downturned lateral side edges 92 and 94 and centrally spaced downwardly extending ribs 96 and 98. Edges 92, 94 and ribs 96, 98 provide spaced support from any surface in that it will be appreciated that cardiac compressor 10 is designed for utilization without support retention 30. It is used on a variety of generally flat surfaces and the ribs and edges provide legs spacing it slightly above such surfaces.

As mentioned previously, legs 46 of intermediate elements 36 includes an offset 50 forming a ridge or shelf 100 extending laterally relative support and retention 30. Shelf 100 supports downwardly turned end or leg 92 of platform 12 and the opposite downwardly turned leg 94 as illustrated in FIG. 4 rides on the bottom portion 56 of intermediate element 46. The height of shelf 100 thus indexes the platform at the proper inclined angle matching that of back support portion 32. The central raised portion 58 of intermediate member 36 has a longitudinal width relative the support and retention 30 which corresponds generally to the spacing of downwardly extending ribs 96 and 98 of platform 12. In effect, the configuration of intermediate member 36 as described, forms a track or guide for platform 12 when it is inserted. Thus, the platform need not be particularly carefully inserted positionwise since the introduction of its free end into either inlet 42 or 44 will be essentially automatically aligned with the platform being positioned at the proper angle of inclination and fully supported at each edge 92, 94 and at its center by projection 58 of intermediate member 36. Projection 58 acts as a lateral stop (i.e. sideways relative to the patient) to locate the platform 110 of the CPR relative the support and patient retainer thereon. Also, it serves as a support for the central portion 60 when manual resuscitation is being performed without base 110 in place.

Although but one embodiment has been shown and described in detail, it will be obvious to those having ordinary skill in this art that the details of construction of this particular embodiment may be modified in a great many ways without departing from the unique concepts presented. It is therefore intended that the invention is limited only by the scope of the appended claims rather than by particular details of the construction shown, except as specifically stated in the claims.

The embodiments of the invention in which an exclusive property or privilege is claimed are defined as follows:

1. A patient cardiopulmonary resuscitative and back retention and support adapted for placement on a generally planar patient body support comprising in combination: a base and upper back support for supporting and raising only a portion of the patient above said patient body support having portions spaced from each other to form an opening and clearance for receipt of an external cardiac compressor platform, said opening extending tranversely of a patient positioned on said back support.

2. The retention and support according to claim 1 wherein said opening and clearance extends laterally to each side permitting insertion of a cardiac compressor platform from either side.

3. A patient cardiopulmonary resuscitative back retention and support comprising in combination: a base and upper back support having portions spaced from each other to form an opening and clearance for receipt of an external cardiac compressor platform, said opening and clearance extending laterally to each side permitting insertion of a cardiac compressor from either side; and wherein said support includes first attachment means for releasably attaching said support to a body support and second attachment means for releasably anchoring a patient to said back support restricting essential relative movement between the patient, body support and said back support without restricting normal chest movement for breathing and external cardiac compression.

4. The back retention and support according to claim 3 wherein said upper back support includes a saddle portion for indexing a patient's back supported thereon.

5. The back retention and support according to claim 4 wherein said saddle portion is inclined upwardly whereby the shoulders of the patient supported thereon are elevated relative the lower body system and the head of the patient is positionable at a downwardly inclined angle from the shoulders providing patency of the breathing canals.

6. A patient cardiopulmonary resuscitative back retention and support comprising in combination: a base and upper back support having portions spaced from each other to form an opening and clearance for receipt of an external cardiac compressor platform, said opening and clearance extending laterally to each side permitting insertion of a cardiac compressor from either side; and wherein said clearance and opening is comprised of an inlet on each side and a central portion, said inlets having a greater cross section than said central portion to facilitate entry of a platform in either of said inlets.

7. The back retention and support according to claim 6 wherein said inlets decline in cross section to said central portion forming a guide means for the entry of a cardiac compressor platform.

8. The back retention and support according to claim 6 wherein said central portion includes an upstanding shoulder which supports at least in part a platform inserted in said clearance, said shoulder being positioned in close proximity to said upper back support for supporting same when used for manual resuscitation.

9. The back retention and support according to claim 8 wherein said shoulder acts as a stop for a related portion on the platform for properly indexing the platform laterally when inserted in said clearance.

10. The back retention and support according to claim 9 wherein said upper back support is inclined upwardly whereby the shoulders of a patient supported thereon are elevated relative the remainder of the body, said central portion of said clearance including means defining a track having a pair of spaced guides, one of said guides being positioned above the other so that when the platform of a cardiac compressor is inserted therein, the platform is inclined in accordance with the inclination of the upper back support.

11. A patient cardiopulmonary resuscitative back retention and support comprising in combination: a base and upper back support having portions spaced from each other to form an opening and clearance for receipt of an external cardiac compressor platform; and wherein said upper back support is inclined upwardly whereby the shoulders of a patient supported thereon are elevated relative the remainder of the body.

12. A portable back support for use during cardiopulmonary resuscitation comprising, in combination: a base; an upper support portion secured to said base and having a portion spaced above said base, said space defining an opening extending laterally to each side of said back support to permit insertion of a cardiac compressor platform in said opening from either side of said back support; and an intermediate generally U-shaped member having a web and upwardly extending leg portions, said web portion being positioned on said flat base and said upwardly extending legs extending up to and supporting said upper support portion to space same from said base.

13. The portable back support according to claim 12 wherein said support is particularly adapted for utilization with a cardiac compressor platform which has a relatively low cross-sectional profile, said platform being generally flat and having a downwardly extending lip along each side which acts as support legs which space the platform above the surface upon which it rests, the transition between said web portion and upstanding legs of said intermediate portion being adapted to support the lip portions of said cardiac compressor platform.

14. The portable back support according to claim 13 wherein said upper support portion is inclined upwardly for supporting the shoulder of the patient thereon so that the shoulders are positioned above the remainder of the body and the head portion of the patient extends downwardly for increased patency of the breathing canals.

15. The portable back support according to claim 14 wherein the forward most leg of said intermediate portion includes a shoulder elevated above the web portion for receiving one of the lips of said cardiac compressor platform for supporting said cardiac compressor platform at an angle of inclination essentially equal to the angle of inclination of said upper support portion.

16. The portable back support according to claim 15 wherein said web portion of said intermediate portion includes a disrupted portion extending upwardly forming a centrally located support for receiving and supporting the central portion of said cardiac compressor platform when inserted therein, said central support being positioned in close proximity to said upper support portion to provide support when said portable back support is utilized for manual resuscitation.

17. The portable back support according to claim 16 wherein said cardiac compressor platform includes an additional pair of downwardly depending spaced ribs extending generally parallel to said lip portions and spaced therefrom to provide central support for said platform when positioned on a support surface, said upwardly extending central support on said web portion being positioned intermediate said ribs when said platform is positioned in said opening.

18. The portable back support according to claim 17 wherein said central support on said web portion provides a stop engageable with means on said cardiac compressor platform to properly locate said platform when inserted in said opening.

19. The portable back support according to claim 12 wherein said base portion includes strap means anchored thereto for securing said portable back support to a cot or the like and said upper support portion includes a pair of spaced strap means securable over the patient's shoulders for connection to strap means anchored to said back support for anchoring the patient's upper body securely to the portable back support without interferring with any movement of the chest of the patient.

20. The portable back support according to claim 19 wherein said upper back support portion has a saddle-like configuration facilitating the position of a patient thereon for resuscitation.

* * * * *